US008183006B2

(12) United States Patent
Ribas De Pouplana et al.

(10) Patent No.: US 8,183,006 B2
(45) Date of Patent: May 22, 2012

(54) SCREENING METHOD FOR IDENTIFYING NEW AMINOACYL-TRNA SYNTHETASE INHIBITORS

(75) Inventors: Lluis Ribas De Pouplana, Barcelona (ES); Teresa Bori Sanz, Barcelona (ES); Manuel Castro De Moura, Lloret de Mar (ES); Renaud Geslain, Barcelona (ES)

(73) Assignees: Fundacio Privada Parc Cientific de Barcelona, Barcelona (ES); Institucio Catalana de Recerca I Estudis Avanca, Barcelona (ES)

( * ) Notice: Subject to any disclaimer, the term of this patent is extended or adjusted under 35 U.S.C. 154(b) by 601 days.

(21) Appl. No.: 12/439,814

(22) PCT Filed: Aug. 30, 2007

(86) PCT No.: PCT/EP2007/059063
§ 371 (c)(1),
(2), (4) Date: Mar. 3, 2009

(87) PCT Pub. No.: WO2008/028862
PCT Pub. Date: Mar. 13, 2008

(65) Prior Publication Data
US 2010/0055719 A1    Mar. 4, 2010

(30) Foreign Application Priority Data
Sep. 4, 2006   (EP) ..................................... 06120049

(51) Int. Cl.
*C12Q 1/48*    (2006.01)
*C12Q 1/02*    (2006.01)
*C12N 9/00*    (2006.01)
(52) U.S. Cl. .............................. 435/15; 435/29; 435/183
(58) Field of Classification Search ........................ None
See application file for complete search history.

(56) References Cited

U.S. PATENT DOCUMENTS
5,798,240 A    8/1998    Martinis et al.

FOREIGN PATENT DOCUMENTS
EP    1251175 A1    10/2002

OTHER PUBLICATIONS

O'Donoghue et al., "On the Evolution of Structure in Aminoacyl-tRNA Synthetases", Microbiology and Molecular Biology Reviews, 2003, 67(4):550-573.*

Beebe et al., "Elucidation of tRNA-dependent editing by a class II tRNA synthetase and signi®cance for cell viability", EMBO J., 2003, 22(3):668-675.*
Weygand-Durašević, Ivana et al., Yeast seryl-tRNA Synthetase Expressed in *Escherichia coli* Recognizes Bacterial Serine-Specific tRNAs in Vivo, Eur. J. Biochem, 1993, pp. 869-877, vol. 214.
Giegé, Richard et al., Universal Rules and Idiosyncratic Features in tRNA Identity, Nucleic Acids Research, 1998, pp. 5017-5035, vol. 26.
Muramatsu, Tomonari et al., Codon and Amino-Acid Specificities of a Transfer RNA are Both Converted by a Single Post-Transcriptional Modification, Nature, 1988, pp. 179-181, vol. 336.
Döring, Volker et al., Enlarging the Amino Acid Set of *Escherichia coli* by Infiltration of the Valine Coding Pathway, Science, 2001, pp. 501-504, vol. 292.
Rai, Meena et al., Expression Systems for Production of Heterologous Proteins, Current Science, 2001, pp. 1121-1128, vol. 80, No. 9.
Edholm, Dan et al., Adenovirus Vector Designed for Expression of Toxic Proteins, J. Virology, 2001, pp. 9579-9584. vol. 75, No. 20.
Sauer, Brian, Cre/lox: One More Step in the Taming of the Genome, Endocrine, 2002, pp. 221-228, vol. 19, No. 3.
Eldred, Emmett W. et al., Rapid Deacylation by Isoleucyl Transfer Ribonucleic Acid Synthetase of Isoleucine-Specific Transfer Ribonucleic Acid Aminoacylated with Valine, J. Biol. Chem., 1972, pp. 2961-2964, vol. 247.
Bishop, Anthony C et al., Interstice Mutations that Block Site-to-Site Translocation of a Misactivated Amino Acid Bound to a Class I tRNA Synthetase, P.N.A.S, 2003, pp. 490-494, vol. 100, No. 2.
Pezo, V. et al., Artificially Ambiguous Genetic Code Confers Growth Yield Advantage, P.N.A.S., 2004, pp. 8593-8597, vol. 101.

(Continued)

*Primary Examiner* — Suzanne M Noakes
(74) *Attorney, Agent, or Firm* — Peter B. Scull; Hamilton, DeSanctis & Cha, LLC (57) ABSTRACT

The method comprising: a) obtaining a gene sequence codifying a naturally occurring aminoacyl-tRNA synthetase; b) engineering the gene codifying for said aminoacyl-tRNA synthetase, resulting into an aminoacyl-tRNA synthetase with a defective activity, with the proviso that the engineering does not affect the functionality of the catalytic site of the enzyme; c) cloning the gene resulting from step (b) in an expression vector; d) transforming isolated mammalian cells with the expression vector resulting from step (c); e) growing the recombinant cells resulting from step (d) in a nutrient medium under conditions which allow the expression of the engineered aminoacyl-tRNA synthetase, resulting the expression into cell death or a decrease in the rate of cell division; f) providing a substance to be tested to the medium resulting from step (e); and g) analyzing the resulting cell growth, wherein if there is an increase in cell growth, then the substance selectively inhibits the activity of the engineered aminoacyl-tRNA synthetase and does not affect to its cellular ortholog, resulting in that said substance is a candidate to drug.

15 Claims, 2 Drawing Sheets

OTHER PUBLICATIONS

Notification of Transmittal of the International Search Report and the Written Opinion of the International Searching Authority, or the Declaration, 19/11/2007, European Patent Office.

Rich, A., RNA Structure and the Roots of Protein Synthesis, Cold Spring Harb. Symp. Quant. Biol., 2001, pp. 1-16, vol. 66.

Lin et al., Laura et al., Aminoacylation Error Correction, Nature, 1996, pp. 33-34, vol. 384.

Bacher et al., Jamie M. et al., Inhibited Cell Growth and Protein Functional Changes from an Editing-Defective tRNA Synthetase, P.N.A.S., 2005, pp. 1697-1701, vol. 102, No. 5.

Eldred et al., Rapid Deacylation by Isoleucyl Transfer Ribonucleic Acid Synthetase of Isoleucine-specific Transfer Ribonucleic Acid Aminoacylated with Valine, J. Biol. Chem., 1972, pp. 2961-2964, vol. 247.

* cited by examiner

SCREENING METHOD FOR IDENTIFYING NEW AMINOACYL-TRNA SYNTHETASE INHIBITORS

The present invention relates to a new screening method which permits the identification of new drugs. Particularly, the present invention refers to a screening method for the selection of aminoacyl-tRNA synthetase inhibitor substances which can be useful as antibacterial and antifungal agents, among others.

BACKGROUND ART

In modern drug discovery programs, chemical libraries are used in combination with robotic systems to rapidly evaluate the effect of large numbers of compounds on a given reaction. This approach has two major drawbacks. First, a biochemical assay that can be easily monitored often needs to be developed in order to identify candidate compounds. This process is costly and insensitive due to potential negative effects of the selected drugs. Secondly, this approach ignores bioavailability and toxicity parameters. In fact, most of the compounds initially selected are later discarded due to solubility, bioavailability, or toxicity problems.

Aminoacyl-tRNA synthetases (hereinafter so-called "ARSs") represent ideal targets for drug development because they are essential enzymes of universal distribution, whose ancestral nature allows for the selection of specific inhibitors. In addition, they are soluble, stable, easy to express and purify in large amounts, and are straightforward to assay by one or more methods. X-ray structures are available for all synthetases, and much is known about the aminoacylation reaction mechanism (cf. Weygand-Durasevic I. et al., "Yeast seryl-tRNA synthetase expressed in *Escherichia coli* recognizes bacterial serine-specific tRNAs in vivo", *Eur. J. Biochem.*, 1993, vol. 214, pp. 869-877).

The genetic code is established in the aminoacylation reactions by the ARSs, where each amino acid is linked to its cognate tRNA that bears the anticodon triplet of the code. The rate of misincorporation of amino acids into proteins is very low (estimated at one error in every $10^5$ codons) and this high accuracy results largely from the precision of aminoacylation reactions. The aminoacylation reaction takes place within a single active site domain and typically proceeds in two steps. First, the amino acid is activated with ATP to form aminoacyl-adenylate with release of pyrophosphate. Next, the amino acid is transferred to the 3'-end of the tRNA to generate aminoacyl-tRNA and AMP. This two-step reaction establishes the genetic code by linking specific nucleotide triplets (tRNA anticodons) with specific amino acids.

The recognition of tRNAs by ARSs depends mostly on molecular interactions with the acceptor stem and the anticodon loop of the tRNA (cf. Rich, A. "RNA structure and the roots of protein synthesis", *Cold Spring Harb. Symp. Quant. Biol.*, 2001, vol. 66, pp. 1-16). The active site domain of the enzyme binds to the acceptor arm of the tRNA molecule, where the amino acid is attached. The 'discriminator' base (the unpaired base that precedes the universal CCA sequence), and the first three base pairs of the acceptor stem harbor most identity elements recognized by ARS active sites. Other domains are used by the enzymes to recognize the anticodon region or other structures of the tRNA. These additional domains are not universally conserved, and can vary from enzyme to enzyme and from species to species.

In addition to tRNA recognition, ARSs must discriminate between amino acids in the cellular pool. In this regard, there are 20 ARSs, each one recognizing a specific amino acid. Generally, amino acids with side chains that are bulkier than those of the cognate amino acids are sterically excluded from the active sites of ARSs, but smaller amino acids can fit into the active site pocket and be misactivated and mischarged. These misactivated adenylates or mischarged tRNAs are normally cleared by the editing function of ARSs. If they are not cleared, genetic code ambiguity is introduced.

Among the translation-directed commercial antibiotics one is targeted to an ARS. Pseudomonic acid (mupirocin) is an inhibitor of isoleucyl-tRNA synthetases (IleRS) from Gram-positive infectious pathogens. Pseudomonic acid has an approximate 8000-fold selectivity for pathogen vs. mammalian IleRS, but the drug's lack of systemic bioavailability limits its use to topical applications.

Although other known natural product inhibitors directed against synthetases exist (e.g., borrelidin, furanomycin, granaticin, etc.), none of these has been developed into commercial antibiotics due to lack of inhibitory activity, poor specificity or poor bioavailability. Thus, a more efficient method for selecting ARS inhibitors is required to screen large chemical libraries and identify promising drug candidates.

SUMMARY OF THE INVENTION

The aim of the present application is to provide a screening method for the selection of ARS inhibitors.

It is provided a screening method which implies that the desired effect of a potential lead substance is the rescue and/or stimulation of the mammalian cell growth, and not the inhibition of any given reaction or the arrest in growth of the cell culture. Thus, in the positive selection that here is proposed, the growth of mammalian cells is rescued by those substances capable of inhibiting the toxic action of a target ARS which has been previously engineered. This effect can be monitored simply by measuring culture density, a fast and cheap procedure.

Thus, an aspect of the present invention is the provision of a screening method for identifying a candidate to drug, said method comprising the steps of: a) obtaining a gene sequence codifying a naturally occurring aminoacyl-tRNA synthetase; b) engineering the gene codifying for said aminoacyl-tRNA synthetase, resulting into an aminoacyl-tRNA synthetase with a defective activity, with the proviso that the engineering does not affect the functionality of the catalytic site of the enzyme; c) cloning the gene resulting from step (b) in an expression vector; d) transforming isolated mammalian cells with the expression vector resulting from step (c); e) growing the recombinant cells resulting from step (d) in a nutrient medium under conditions which allow the expression of the engineered aminoacyl-tRNA synthetase, resulting the expression into cell death or a decrease in the rate of cell division; f) providing a substance to be tested to the medium resulting from step (e); and g) analyzing the resulting cell growth, wherein if there is an increase in cell growth, then the substance selectively inhibits the activity of the engineered aminoacyl-tRNA synthetase and does not affect to its cellular ortholog, resulting in that said substance is a candidate to drug.

In this manner, using engineering techniques the enzyme looses the specificity of uniquely ligating the cognate amino acid to its cognate tRNA. Thus, when the tRNA bearing aminoacylation mistakes is produced, the modified protein becomes toxic to the mammalian host cell, this toxicity giving rise to a reduction in the rate of cell division growth or to cell death. When the substance to be tested is provided to the cell culture media, it can interact with the catalytic site of the engineered ARS, inhibiting this enzyme (i.e., inhibiting the production of mutated proteins which are toxic for the host cell). Consequently, the cell growth is rescued since no more toxic proteins are produced and it can be confirmed that the administered substance is a candidate to drug. This is due to the fact that the catalytic site of the engineered ARS has not been manipulated and, therefore, the substance that binds to the active site of the engineered enzyme is also able to bind to the one of the wild-type ARS of pathogenic origin and, hence, becomes a candidate to drug for the treatment of an illness caused by the pathogen.

The ability of the substance to selectively discriminate between the ARS with defective activity and the ortholog ARS of the transfected mammalian cell can be estimated, for instance, by measuring the capacity of the substance to inhibit the incorporation of radioactive amino acids to its cognate tRNA, and comparing this activity to the ability of the same substance to inhibit the activity of the corresponding mammalian enzymes on their respective cognate tRNAs. A substance is specific when it can inhibit the enzyme from the pathogen, but not the corresponding mammalian enzyme.

Consequently, the substance is tested for its ability to inhibit the growth of the organism from which the ARS is engineered in order to obtain a defective ARS. The substance that displays selective inhibition of the defective ARS and the ability to retard or stop the growth of the organism that naturally contains the original ARS is considered a potential drug candidate useful to inhibit the growth this organism.

Advantageously, the substances identified as drug candidates following the screening method of the present invention are characterized as being small molecules selected due to their ability to revert the toxic effect of the engineered ARS, but also as being able to, simultaneously, cross the cellular membrane, inhibit the foreign synthetase, not inhibit its human ortholog, and not affect other aspects of the cell metabolism. Therefore, the screening method of the present invention permits the identification of a drug candidate which specifically inhibits the foreign ARS synthetase and is not toxic for the host cell, being no needed additional assays of toxicity.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and variations of the word, such as "comprising", are not intended to exclude other technical features, additives, components, or steps. Additional objects, advantages and features of the invention will become apparent to those skilled in the art upon examination of the description or may be learned by practice of the invention. The following examples and drawings are provided by way of illustration, and are not intended to be limiting of the present invention.

DETAILED DESCRIPTION OF PARTICULAR EMBODIMENTS

As used herein, the expression "with a defective activity" related to the aminoacyl-tRNA synthetase refers to the partial or total loss of the aminoacyl-tRNA synthetase's ability to link the specific amino acid to its cognate tRNA, once it has been submitted to well-known engineering techniques for the skilled man in the art, resulting in the aminoacylation of tRNA with amino acids other than the natural cognate amino acid for the tRNAs. There are no restrictions regarding the engineering technique to be used with the proviso that the catalytic site of the enzyme (wherein the ligation of the amino acid to the tRNA is carried out) is no mutated. Illustrative, non-limiting examples are: site-directed mutagenesis, random mutagenesis followed by genetic selection and phage display techniques, among others.

The simultaneous expression of the genes coding for the engineered naturally occurring tRNA synthetase and its tRNA substrate can increase the ability of the said tRNA synthetase to induce toxicity in the cells that express both genes.

Thus, in one embodiment of the first aspect of the invention the expression vector obtained in step (c) also comprises a gene sequence codifying for a tRNA substrate of the naturally occurring pathogenic non-discriminating tRNA synthetase.

In another embodiment of the first aspect of the invention the mammalian cells are transformed in step (d) using a second expression vector comprising a gene sequence codifying for a tRNA substrate of the naturally occurring pathogenic non-discriminating tRNA synthetase.

Gene sequences codifying for a tRNA substrate of naturally occurring pathogenic non-discriminating tRNA synthetases are available from public databases (*Helicobacter pylori* complete genome sequences from three different isolates can be found under Genebank references NC_000915.1, NC_008086.1, and NC_000921.1).

The naturally occurring aminoacyl-tRNA synthetases, which are well-known for the skilled man in the art, are the valyl-, isoleucyl-, cysteinyl-, leucyl-, methionyl-, tyrosyl-, tryptophanyl-, glutamyl-, glutaminyl-, arginyl-, alanyl-, threonyl-, seryl-, prolyl-, glycyl-, histidyl-, aspartyl-, lysyl-, asparaginyl-, and phenylalanyl-tRNA synthetases and any of them can be engineered in order to make them activity-defective (cf. Giegé, R. et al., "Universal rules and idiosyncratic features in tRNA identity", *Nucleic Acids Research*, 1998, vol. 26, pp. 5017-5035).

In one embodiment of the present invention, the aminoacyl-tRNA synthetase resulting from step (b) is defective in the recognition of its cognate tRNA.

As used herein, the term "aminoacyl-tRNA synthetase is defective in the recognition of the tRNA" or "recognition-defective ARS" refers to an aminoacyl-tRNA synthetase whose tRNA recognition domains have been modified in such a way that the recognition specificity has been reduced or altered, without affecting the catalytic site domain of said aminoacyl-tRNA synthetase. The modification of the tRNA specificities of several ARSs has been achieved. Illustrative non-limiting examples are those modifications based mainly on changes in the anticodon binding domains of these proteins. For example, the recognition of the anticodon by IleRS and MetRS can be manipulated to force IleRS to recognize tRNA$^{Met}$ and MetRS to do the same with tRNA$^{Ile}$ (cf. Muramatsu, T. et al., "Codon and amino-acid specificities of a transfer RNA are both converted by a single post-transcriptional modification", Nature, 1988, vol. 336, pp. 179-181).

The recognition of tRNAs by ARSs depends mostly on molecular interactions with the acceptor stem and the anticodon loop of the tRNA. The 'discriminator' base (the unpaired base that precedes the universal CCA sequence), and the first three base pairs of the acceptor stem harbor most identity elements recognized by ARS active sites. Other domains are used by the enzymes to recognize the anticodon region or other structures of the tRNA. These additional domains are not universally conserved, and can vary from enzyme to enzyme and from species to species. When the ARS is engineered, resulting in a recognition-defective ARS and it is introduced into a mammalian cell, a toxicity into the cell can be observed. In this manner, when the ARS is engineered there is a total or partial loss of the specificity in the recognition of the cognate tRNA, being no possible to ligate the specific amino acid to its cognate tRNA, resulting in the production of tRNAs aminoacylated with incorrect amino acids. The main consequence is that there can be a massive mutagenesis in the proteins synthesized by the cell, generating a toxic effect which gives rise to cell death or a reduction into the cell division growth.

In another embodiment of the present invention, the naturally occurring aminoacyl-tRNA synthetase of step (a) has an editing activity and the aminoacyl-tRNA synthetase resulting from step (b) is editing-defective.

As used herein, the term "editing aminoacyl-tRNA synthetase" or "naturally occurring aminoacyl-tRNA synthetase having an editing activity" refers to the aminoacyl-tRNA synthetases containing along with the recognition site which catalyzes aminoacyl-adenylate formation and tRNA aminoacylation (which is common to all the aminoacyl-tRNA synthetases), an editing or proof-reading site which hydrolyzes misactivated adenylates or mischarged tRNAs. The editing activity is in an additional domain attached to the core domains of the enzyme (cf. Lin L. et al., "Aminoacylation error correction", Nature, 1996, vol. 384, pp. 33-34). The combined activities of these two sites lead to rigorous accuracy in tRNA aminoacylation, avoiding that amino acids similar to the target amino acid are ligated to the tRNA. The aminoacyl-tRNA synthetases with an editing activity are the isoleucyl-, valyl-, leucyl, methionyl-, alanyl-, threonyl-, prolyl- and phenylalanyl synthetases and are well-known for those skilled men in the art.

For instance, isoleucyl-tRNA synthetase can ligate valine instead of its natural substrate isoleucine, because these two amino acids differ only in one single methyl group. In order to prevent the formation of valine-tRNA$^{Ile}$, the enzyme recognizes this mistaken product or the mistaken reaction intermediate through its editing activity and hydrolyzes them, releasing the valine from the tRNA. Thus, the isoleucyl-tRNA synthetase (abbreviated "IleRS") may start the aminoacylation reaction by activating valine (the wrong substrate) with ATP to form a valyl-adenylate as the intermediate step to aminoacrylate tRNA$^{Ile}$. The reaction may continue and tRNA$^{Ile}$ may be misacylated by the enzyme to form Val-tRNA$^{Ile}$ (Equation 1). Then, the misactivated valine in the form of valine-adenylate, or the mischarged valine-tRNA$^{Ile}$, would be hydrolyzed by the editing site of the enzyme, thus avoiding its ulterior use to produce a protein which is toxic for the cell (Equation 2):

$$Val+ATP+IleRS \rightarrow IleRS(valine-AMP)+Ppi\ IleRS$$
$$(valine-AMP)+tRNA^{Ile} \rightarrow valine-tRNA^{Ile}+$$
$$AMP+IleRS \quad (Eq.\ 1)$$

$$IleRS(valine-AMP) \rightarrow IleRS+valine+AMP\ valine-$$
$$tRNA^{Ile}+IleRS \rightarrow valine+tRNA^{Ile}+IleRS (Eq.\ 2)$$

As used herein, the term "editing-defective" refers to an aminoacyl-tRNA synthetase whose editing site has been modified in such a way that the editing activity has been reduced or removed without being affected the recognition site. In order to reduce or remove the editing activity of the aminoacyl-tRNA synthetases, ordinary engineering techniques can be used, for instance site-directed mutagenesis (cf. Doring, V. et al., "Enlarging the amino acid set of Escherichia coli by infiltration of the valine coding pathway", Science, 2001, vol. 292, pp. 453-454).

The introduction of an editing-defective ARS into a mammalian cell results in the formation of mischarged tRNAs which can not be hydrolized by the enzyme as being defective in its editing activity. The main consequence is that there can be a massive mutagenesis in the proteins synthesized by the cell, generating a toxic effect which gives rise to cell death or a reduction into the cell division growth.

This toxic effect may be enhanced by increasing the concentration of those amino acids that are mistakenly used by the editing-defective ARS in the media used to cultivate the mammalian cells expressing the editing-defective aminoacyl-tRNA synthetases.

The cell death caused by aminoacyl-tRNA synthetases with a defective activity can be monitored by a variety of commercial or standard methods (neutral red uptake, WST1, LDH levels, ATP levels, and others), using spectrophotometers or any other device designed for the purpose of monitoring cell death.

In the present invention "an expression vector" refers to a carrier molecule to which a desired segment of DNA (e.g. heterologous nucleic acid) is inserted. The vector serves to incorporate foreign DNA into host cells. More particularly, an "expression vector" is a DNA vector containing a DNA sequence which is operably linked to a suitable control sequence capable of affecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome either itself generating stable cell lines that express said gene constitutively or after the treatment of the cells with an inducer of the expression of the gene. The terms "plasmid" and "vector" are sometimes used interchangeably herein, because the plasmid is the most commonly used form of vector at present. However, the invention is intended to include such other forms of vector that serve an equivalent function and are or become known in the art.

Expression vectors typically further contain other functionally important nucleic acid sequences, such as expression cassettes encoding antibiotic resistance proteins, multiple cloning sites, replication sequences, and the like.

In one embodiment of the present invention, the expression vector is selected from the group consisting of a viral or non-viral plasmid, cosmid, phagemid, shuttle vector, yak, and the like. Preferably the expression vector is an adenovirus.

In another embodiment of the present invention, the vector further comprises a tetracycline-dependent regulation system for the expression of the gene.

In still another embodiment of the invention the vector comprises a selection marker. Preferably the selection marker is hygromicine.

In still yet another embodiment, the aminoacyl-tRNA synthetase naturally occurring comes from bacteria, fungus, protozoa and metazoan.

As used herein, the terms "transformation" and "transfection" refer to any of the variety of art-recognized techniques for introducing foreign nucleic acid (e.g. DNA) into either a prokaryotic or eukaryotic host cell (including isolated human cells). Suitable means for introducing (transducing) expression vectors containing nucleic acid into host cells to produce transduced recombinant cells, or to generate stable cell lines containing the gene integrated in the nuclear DNA of the cells are well-known in the art. Suitable methods for transforming or transfecting host cells can be found in Molecular Cloning: A Laboratory Manual, 3rd edition, edited by J. Sambrook and D. W. Russell (Cold Spring Harbor Laboratory Press, Cold Spring Harbor, N.Y., 2000), and other laboratory manuals.

Methods for the growth and preservation of bacterial strains are disclosed in Molecular Cloning: A Laboratory Manual, 3rd edition, edited by J. Sambrook and D. W. Russell (Cold Spring Harbor Laboratory Press, 2000). Controlling the expression of genes in human cells and repressing the existence of basal expression can be challenging as it is well-known for the skilled person in the art (cf. Rai et al., "Expression systems for production of heterologous proteins", *Current Science,* 2001, vol. 80, pp. 1121-11). The inventors have taken advantage of two recent developments in the field of protein expression of human cells to construct our tester strains. First, it has been used an adenovirus-based gene expression vector based on the tetracycline-regulated Tet-ON- and the progesterone antagonist RU 486-regulated gene expression systems. This vector can function in a number of cell types and the regulation of protein expression was shown to be tightly controlled (cf. Edholm, D. et al., "Adenovirus vector designed for expression of toxic proteins", *J. Virology,* 2001, vol. 75, pp. 9579-9584).

Alternatively, the construction of tester strains can be based on the Cre/loxP recombination system for the activation of gene transcripts. Cre is a 38 kDa recombinase protein from bacteriophage P1 which mediates intramolecular (excessive or inversional) and intermolecular (integrative) site specific recombination between loxP sites. The Cre's DNA excising capability can be used to turn on a foreign gene by cutting out an intervening stop sequence between the promoter and the coding region of the gene. Thus, the genes coding for the toxic synthetases could be introduced in human cells in a vector whose transcription initiation site is blocked by a stop signal. The recombination, i.e. excision of the stop signal, occurs only when the expression of Cre is activated (cf. Sauer, B et al., "Cre/lox: one more step in the taming of the genome", *Endocrine,* 2002, Vol. 19, pp. 221-228).

Once the tester strains are developed the inventors have designed a simple growth-monitoring test in 96-well plates using an automatic plate reader. They have already managed to implement a similar procedure for the analysis of the toxic enzymatic effect in *E. coli*. Once this test is operational it is started the screening of small molecule libraries to look for potential new inhibitors of target synthetases.

The terms "test substance" and "substance" are used interchangeably and refer to a compound, a mixture of compounds (i.e., at least two compounds), or a natural product sample containing one or more compounds.

Short of testing the effect of small substances in whole tissues or individuals, testing them in human cell cultures may provide the screens with the highest possible discriminatory power, because the selection based on cell growth identifies compounds or combinations of compounds on a multi-factorial basis. Initial selections identify inhibitors capable of blocking the activity of the synthetase and of traversing cellular membranes, while the second screen further refine the search for substances that did not affect human cells metabolism.

Substances to be tested for their ability to eliminate the toxic effect caused by editing-defective aminoacyl-tRNA synthetases are added to the cells before, during, or after the induction of the expression of the genes coding for the editing-defective aminoacyl-tRNA synthetases. After inducing the expression of the genes, the cell death is monitored in each culture in the presence or absence of the substance to be tested.

The substances that cause a reduction in the rate of cell death of the culture with respect to the rate of cell death of the same culture in the absence of the substance are considered potential inhibitors of the editing-defective aminoacyl-tRNA synthetases that cause cell death.

Thus, in one embodiment of the present invention the aminoacyl-tRNA synthetase is obtained from a bacterium, and the substance is being tested to determine whether it is an antibacterial agent.

In another embodiment of the present invention the aminoacyl-tRNA synthetase is obtained from a fungus, and the substance is being tested to determine whether it is an antifungal agent.

In another embodiment of the present invention the aminoacyl-tRNA synthetase is obtained from a protozoan, and the substance is being tested to determine whether it is an anti-parasite agent.

In another embodiment of the present invention the aminoacyl-tRNA synthetase is obtained from a metazoan, and the substance is being tested to determine whether it is an anti-metazoan agent.

As will be appreciated by those in the art, the type of mammalian cells used in the present invention can vary widely. Basically, any mammalian cells may be used, with mouse, rat, primate and human cells being particularly preferred. More preferably, the isolated mammalian cells are human.

EXAMPLES

The pathogenic bacterium *Streptococcus pneumoniae* utilizes one essential isoleucyl-tRNA synthetase (IleRS). IleRS is an editing aminoacyl-tRNA synthetase, and its editing reaction is essential to prevent the production of misacylated valine-tRNA$^{Ile}$ by this enzyme (cf. Eldred, E. W & Schimmel, P. R., "Rapid deacylation by isoleucyl transfer ribonucleic acid synthetase of isoleucine-specific transfer ribonucleic acid aminoacylated with valine.", J. Biol. Chem., 1972, vol. 247, pp. 2961-2964).

To investigate whether expression IleRS of *S. pneumoniae*, containing mutations that inactivate the editing activity of this enzyme, has a toxic effect in a mammalian system and leads to cell death, *S. pneumoniae* Isoleucyl-tRNA synthetase whose editing activity was destroyed (and which is abbreviated hereinafter as "IleRSTA"), was fused to green fluorescent protein. The resulting construction was expressed in HeLa cells, a human cell line and its putative toxic effect was examined with increasing concentrations of valine in the culture media.

Production of an Expression Vector Containing the Isoleucil-tRNA Synthetase from *S. pneumoniae*

The whole gene coding for wild-type Isoleucyl-tRNA synthetase of *S. pneumoniae* is accessible from the NCBI DNA sequence database with the accession number AE008519. This gene was amplified from purified genomic DNA from *Streptococcus pneumoniae* (provided by Dr. Petra Zwijnenburg, from the University of Netherlands Medical Science Center, Amsterdam) by the Polymerase Chain Reaction (PCR) method using two DNA primers:

```
IRS#1 (SEQ ID NO: 1)
(5'-GCATGCAACTCAAAGACACC)
and

IRS#2 (SEQ ID NO: 2)
(5'-AGATCTTTTCTCTTCAAATCCTTCTGC)
```

The product of this amplification was then cloned directly into plasmid PCR2.1-TOPO/TA (Invitrogen) for its posterior manipulation.

The gene coding for green fluorescent protein (provided by Dr. Antonio Zorzano, Barcelona Institute for Biomedical Research, Barcelona) was amplified by PCR using the following primers:

```
GFP- IRS #1 (SEQ ID NO: 3)
(5'CATAGGATCCCCACCATGGTGAGCAAGGGCGAGGAG)
and

GFP- IRS #2 (SEQ ID NO: 4)
(5'-CAAGATTAAGGGTGTCTTTGAGTTTCTTGTACAGCTCGTCCATG
CCGAG)
```

Once the GFP gene was amplified, it was fused to the amplified Isoleucyl-tRNA synthetase gene by incubating both PCR products with the oligonucleotide linkers:

```
GFP- IRS #3 (SEQ ID NO: 5)
(5'-CTCGGCATGGACGAGCTGTACAAGAAACTCAAAGACAC
CCTTAATCTTG)
and GFP- IRS#4 (SEQ ID NO: 6)
(5'-GTATGCGGCCGCTTAATGGTGATGGTGATGATGTTTCTCTTCAAAT
C).
```

The resulting product was subsequently mixed together with primers GFP-IRS#1 (SEQ ID NO:3) and GFP-IRS #4 (SEQ ID NO: 6), and a secondary overlap PCR was performed. The final amplified product was cloned into PCR2.1-TOPO/TA (Invitrogen).

The final vector was digested with NotI and the resulting product inserted into similarly cut mammalian expression vector, pCMV (BD Biosciences Clontech).

Mutagenesis of the Gene Coding for IleRS in Order to Destroy the Editing Activity of the Synthetase It has been previously reported that alanine substitutions in a threonine-rich peptide in the IleRS editing domain generated variants of IleRS that are diminished in their editing activity (cf. Pezo, V. et al., "Artificially ambiguous genetic code confers growth yield advantage", *P.N.A.S.*, 2004, Vol. 101, pp. 8593-8597). Site-directed mutagenesis of IleRS to alter its editing domain substituting residues T231, T232, and T233 (as found in the NCBI protein sequence database with the accession number Q9ZHB3) by alanines. The codons corresponding to the mutated amino acids are: (A691,C692, A693), (A694,C695,G696) and (A697,C698,T699). The site-directed mutagenesis was performed using QuickChange site-directed mutagenesis Kit (Stratagene) using the following mutant oligonucleotide primers,

```
IRSTA#1 (SEQ ID NO: 7)
(5'-GTTGTCTGGGCAGCGGCTCCATTTACCATC)
and

IRSTA#2 (SEQ ID NO: 8)
(5'-GATGGTAAATGGAGCCGCTGCCCAGACAAC).
```

This mutagenesis reaction produced a gene coding for the mutated IleRS (IleRSTA).

The integrity and authenticity of both the DNA constructs including the IleRS and the one including the IleRSTA were confirmed by nucleotide sequence.

Cell Culture

HeLa cells (ATCC reference CCL-2) were grown in DMEM medium supplemented with 100 U/ml of penicillin, 100 µg/mL streptomycin and 10% heat-inactivated fetal bovine serum (from Gibco) under 5% $CO_2$/95% air in humidified incubator. Cells were kept at exponential phase of growth. Adherent cells were detached by incubating with tyrosine-EDTA solution for 5 minutes at 37° C. before washing.

Transient and Stable Transfections

For transient transfections, 20 µg of each DNA construct was added to 500 µl water containing 252 mM $CaCl_2$. Then, 500 µl of 2×Hepes-buffered-saline buffer (280 mM NaCl, 10 mM KCl, 1.5 mM $Na_2HPO_4$, 50 mM HEPES, 12 mM dextrose, pH 7.1) was added to the DNA mixture drop by drop. 16 hours after adding this transfection mixture to the cells, the medium containing DNA was removed and new medium was added. After 24 hours, transfected cells were used for experimentation.

For stable transfections, 48 hours after transfection, cells were split in 24-well plates and 500 µg/mL of G418 for selection was added. Approximately, 15 days later, individual clones of cells were selected and put in 96-well plates for expansion. Clones were selected by checking expression GFP by flow cytometry.

Immuno-Blotting

Whole protein extracts of the transfected cells were incubated with Laemmli blue sample buffer and were loaded and separated by SDS-PAGE on 8% gels. Gels were transferred to PVDF membranes (Amersham) and blocked with TBS-T (0.5 M Tris, 1.5 M NaCl), 0.1% (v/v) Tween-20, pH 7.4) containing 10% (w/v) milk for at least 1 hour. Subsequently blots were incubated with purified anti-green fluorescent protein rabbit polyclonal antibody (Immunokontact) at 1:5000 in 10% BSA/TBS-T blocking solution. Blots were washed twice immediately following incubation with primary antibody and then another two times at 15 minutes intervals. Finally blots were incubated with secondary antibody (anti-rabbit IgG, horseradish peroxidase linked whole antibody which was supplied by Amersham) at 1:10000 in TBS-T for 1 hour before washing as before and development using an enhanced chemiluminescence (ECL) detection system (Amersham).

Flow Cytometry Studies

10 µg/ml propidium iodide was used for determination of cell viability in transiently GFP fusion proteins transfected HeLa cells. Stained cells were analyzed immediately using a Coulter Epics XL (Beckman Coulter) and analyzed using System II software.

Results

1. Wild Type and Mutated Editing Domain GFP-IleRS is Expressed in Hela Cells

Figure 1:
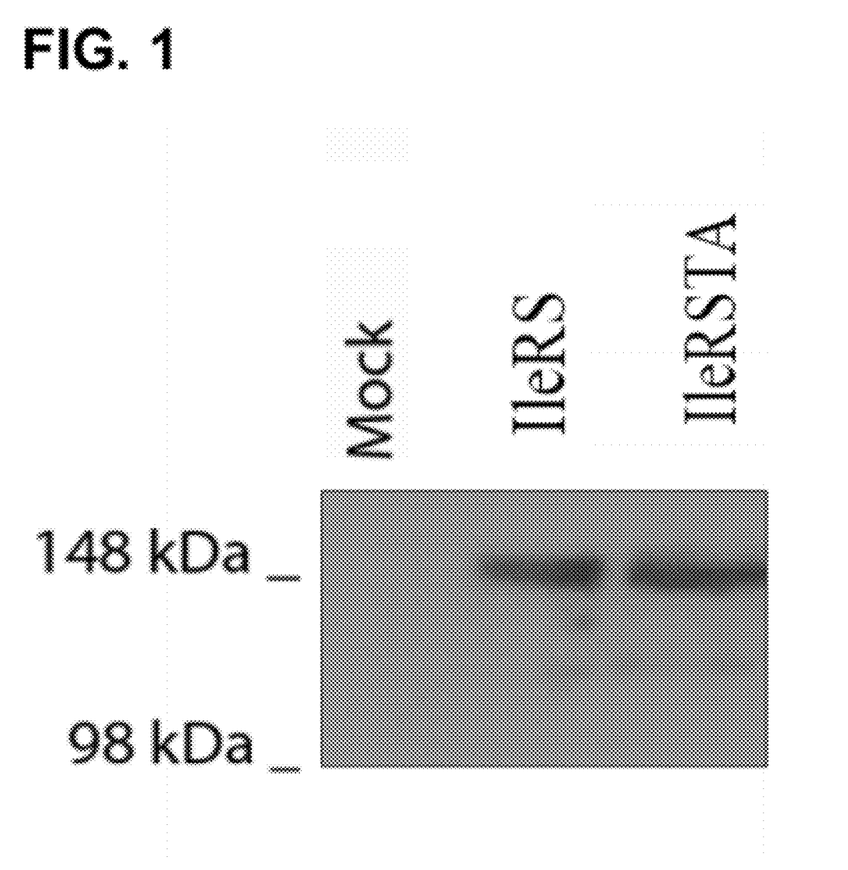
FIG. 1 shows the detection by immunoblotting of the wild-type Isoleucyl-tRNA synthetase (IleRS) from *S. pneumoniae* as well as its expression, once engineered, being an editing-defective Isoleucyl-tRNA synthetase (IleRSTA) in HeLa cells. The "Mock" line corresponds to cells not harbouring either of the two plasmids used.

HeLa cells (from human cervical carcinoma) were transiently transfected with empty plasmid (mock) or plasmid encoding *S. pneumoniae* wild type (pTBGFP-IleRS) and mutated editing domain GFP-IleRS (pTBGFP-IleRSTA). Expression of GFP fusion protein was detected by immunoblotting using anti-GFP polyclonal antibody, as shown in FIG. 1. A band of approximately 148 kDa was detected in wild type (WT) and mutated editing domain (TA) S. pneumoniae GFP-IleRS expressing HeLa cells.

This results demonstrates that S. pneumoniae wild type and mutated editing domain IleRS can be expressed in a human cell line.

2. Expression of IleRSTA Leads to an Increase of Cell Death

To assess whether the expression S. pneumoniae mutated editing domain GFPIleRS has a toxic effect in a mammalian system in the presence of increasing concentrations of valine in the media, GFP, S. pneumoniae wild type (IleRS) and mutated editing domain (IleRSTA) were expressed in HeLa cells.

Figure 2:
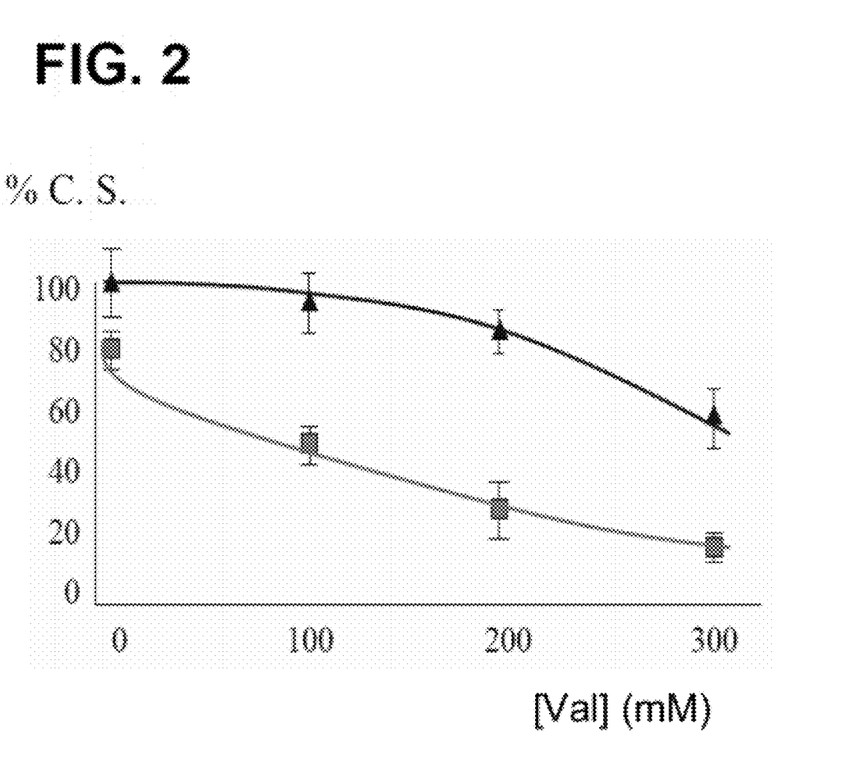
FIG. 2 shows the toxicity caused by increasing concentrations of valine in HeLa cells expressing the wild-type Isoleucyl-tRNA synthetase (▲) and the editing-defective isoleucyl-tRNA synthetase (■). Cell death was measured by propidium iodide staining. Axis y represents the percentage of cell survival (abbreviated as "% C.S.") and axis x represents the concentration of valine (mM).

S. pneumoniae mutated editing domain IleRSTA appears to attribute to a higher sensitivity in the presence of higher concentrations of valine in the media, compared to S. pneumoniae wild type IleRS or GFP expressing HeLa cells as it is illustrated in FIG. 2.

This increase in cell death sensibility may be due to an increase of the misincorporation of valine that, in turn, causes an increased level of misfolded or unfolded proteins in the mutant GFPIleRS expressing cells, leading to an increase of cell death.

Determination of a Candidate Drug

In order to determine if a substance is a candidate drug, this must allow or improve the growth of human cells in the presence of IleRSTA (i.e., this substance must have an inhibitory activity against said editing-defective ARS).

It is carried out a biochemical reaction wherein the GFP-IleRS catalyzes the incorporation of isoleucine to the cognate tRNA. This incorporation is monitored using a radioactively labeled amino acid, and measuring the addition of the radioactive label to the tRNA molecule.

Then, the substance candidate to drug is added to the reaction mixture. The ability of the substance to selectively discriminate between the editing-defective ARS and its human homologue is estimated by measuring the capacity of the substance to inhibit the incorporation of the radioactive amino acid to its cognate $tRNA^{Ile}$, and comparing this activity to the ability of the same substance to inhibit the activity of similar human enzymes on their respective cognate tRNAs. A substance is specific when it can inhibit the enzyme from the pathogenic, but not the similar human enzymes.

Consequently, the substance is tested for its ability to inhibit the growth of the organism that originally contains the ARS used to construct an editing-defective ARS. The substance that displays selective inhibition of the editing-defective ARS and the ability to retard or stop the growth of the organism that naturally contains the original ARS is considered a potential drug candidate useful to inhibit the growth this organism.

The invention claimed is:

1. A screening method for identifying a candidate drug wherein said method comprises the following steps:
   a) obtaining a gene sequence encoding a naturally occurring aminoacyl-tRNA synthetase;
   b) engineering the gene sequence encoding said aminoacyl-tRNA synthetase, resulting in an aminoacyl-tRNA synthetase with a defective activity, with the proviso that the engineering does not affect the functionality of the catalytic site of the enzyme wherein the ligation of the amino acid to the tRNA is carried out;
   c) cloning the gene resulting from step (b) in an expression vector;
   d) transforming isolated mammalian cells with the expression vector resulting from step (c);
   e) growing the recombinant cells resulting from step (d) in a nutrient medium under conditions which allow the expression of the engineered aminoacyl-tRNA synthetase, the expression resulting in cell death or a decrease in the rate of cell division;
   f) providing a substance to be tested to the medium resulting from step (e); and
   g) analyzing the resulting cell growth, wherein if there is an increase in cell growth, then the substance selectively inhibits the activity of the engineered aminoacyl-tRNA synthetase and does not affect its cellular ortholog, resulting in that said substance is a candidate drug;
   wherein the naturally-occurring aminoacyl-tRNA synthetase is isoleucyl-tRNA synthetase (IleRS), and the IleRS is engineered to alter its editing domain by substituting residues corresponding to *Streptococcus pneumonia* Thr231, Thr232 and Thr233 with alanine.

2. The screening method according to claim 1, wherein the expression vector used in step (c) also comprises a gene sequence encoding for a tRNA substrate of the naturally occurring aminoacyl-tRNA synthetase.

3. The screening method according to claim 1, wherein the mammalian cells are transformed in step (d) using a second expression vector further comprising a gene sequence encoding for a tRNA substrate of the naturally occurring tRNA synthetase.

4. The screening method according to claim 1, wherein the naturally occurring aminoacyl-tRNA synthetase of step (a) has an editing activity and the aminoacyl-tRNA synthetase resulting from step (b) is editing-defective.

5. The screening method according to claim 1, wherein the aminoacyl-tRNA synthetase is engineered by site-directed mutagenesis.

6. The screening method according to claim 1, wherein the expression vector is selected from the group consisting of a viral or non-viral plasmid, cosmid, phagemid, shuttle vector and yak.

7. The screening method according to claim 6, wherein the expression vector is an adenovirus vector.

8. The screening method according to claim 6, wherein the vector comprises a tetracycline-dependent regulation system for the expression of the gene.

9. The screening method according to claim 6, wherein the vector comprises a selection marker.

10. The screening method according to claim 9, wherein the selection marker is hygromycin.

11. The screening method according to claim 1, wherein the aminoacyl-tRNA synthetase comes from a bacterium and the substance is being tested to determine whether it is an antibacterial agent.

12. The screening method according to claim 1, wherein the tRNA synthetase comes from a fungus and the substance is being tested to determine whether it is an antifungal agent.

13. The screening method according to claim 1, wherein the tRNA synthetase comes from a protozoan and the substance is being tested to determine whether it is an antiparasite agent.

14. The screening method according to claim 1, wherein the tRNA synthetase comes from a metazoan and the substance is being tested to determine whether it is an antimetazoan agent.

15. The screening method according to claim 1 wherein the isolated mammalian cells are isolated human cells.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: PCR Primer

<400> SEQUENCE: 1
gcatgcaact caaagacacc                                              20

<210> SEQ ID NO 2
<211> LENGTH: 27
<212> TYPE: DNA
<213> ORGANISM: Artificial
<220> FEATURE:
<223> OTHER INFORMATION: PCR Primer

<400> SEQUENCE: 2
agatcttttc tcttcaaatc cttctgc                                      27

<210> SEQ ID NO 3
<211> LENGTH: 36
<212> TYPE: DNA
<213> ORGANISM: Artificial
<220> FEATURE:
<223> OTHER INFORMATION: PCR primer

<400> SEQUENCE: 3
cataggatcc ccaccatggt gagcaagggc gaggag                            36

<210> SEQ ID NO 4
<211> LENGTH: 49
<212> TYPE: DNA
<213> ORGANISM: Artificial
```

```
<220> FEATURE:
<223> OTHER INFORMATION: PCR primer

<400> SEQUENCE: 4
caagattaag ggtgtctttg agtttcttgt acagctcgtc catgccgag                49

<210> SEQ ID NO 5
<211> LENGTH: 49
<212> TYPE: DNA
<213> ORGANISM: Artificial
<220> FEATURE:
<223> OTHER INFORMATION: oligonucleotide linker

<400> SEQUENCE: 5
ctcggcatgg acgagctgta caagaaactc aaagacaccc ttaatcttg                49

<210> SEQ ID NO 6
<211> LENGTH: 47
<212> TYPE: DNA
<213> ORGANISM: Artificial
<220> FEATURE:
<223> OTHER INFORMATION: oligonucleotide linker

<400> SEQUENCE: 6
gtatgcggcc gcttaatggt gatggtgatg atgtttctct tcaaatc                  47

<210> SEQ ID NO 7
<211> LENGTH: 30
<212> TYPE: DNA
<213> ORGANISM: Artificial
<220> FEATURE:
<223> OTHER INFORMATION: oligonucleotide primer to carry out
     site-directed mutagenesis

<400> SEQUENCE: 7
gttgtctggg cagcggctcc atttaccatc                                     30

<210> SEQ ID NO 8
<211> LENGTH: 30
<212> TYPE: DNA
<213> ORGANISM: Artificial
<220> FEATURE:
<223> OTHER INFORMATION: oligonucleotide primer to carry out
     site-directed mutagenesis

<400> SEQUENCE: 8
gatggtaaat ggagccgctg cccagacaac                                     30
```